(12) United States Patent
Marks et al.

(10) Patent No.: US 8,497,387 B2
(45) Date of Patent: Jul. 30, 2013

(54) PROCESS FOR PREPARING DIVINYLARENE DIOXIDES

(75) Inventors: Maurice J. Marks, Lake Jackson, TX (US); Gyongyi Gulyas, Lake Jackson, TX (US); Kevin A. Frazier, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 97 days.

(21) Appl. No.: 13/133,510

(22) PCT Filed: Nov. 23, 2009

(86) PCT No.: PCT/US2009/065435
§ 371 (c)(1),
(2), (4) Date: Jun. 8, 2011

(87) PCT Pub. No.: WO2010/077483
PCT Pub. Date: Jul. 8, 2010

(65) Prior Publication Data
US 2011/0251412 A1    Oct. 13, 2011

Related U.S. Application Data

(60) Provisional application No. 61/141,457, filed on Dec. 30, 2008.

(51) Int. Cl.
*C07D 301/12* (2006.01)
*C07D 301/06* (2006.01)

(52) U.S. Cl.
USPC .......................................... 549/533; 549/531

(58) Field of Classification Search
USPC .................................. 549/531, 533
See application file for complete search history.

(56) References Cited

U.S. PATENT DOCUMENTS

| | | | |
|---|---|---|---|
| 3,635,841 A | 1/1972 | Keith et al. | |
| 5,155,247 A | 10/1992 | Herrmann et al. | |
| 5,463,090 A * | 10/1995 | Rodriguez et al. | 549/531 |

FOREIGN PATENT DOCUMENTS

| | | |
|---|---|---|
| JP | 09286750 | 4/1997 |
| WO | 9620233 | 7/1996 |
| WO | 9800413 | 1/1998 |

OTHER PUBLICATIONS

Inoue et al., Effect of Anions on the Epoxidation of Styrenes with H2O2 in the Presence of Ammonium Heptamolybdate(VI)-Dioctyltin Oxide Catalysts, Bulletin Chemical Society Japan, 64, pp. 3442-3444, 1991.
Srinivas et al., Biomimetic Oxidations Using Transition Metal Complexes Encapsulated in Zeolites, Catalysis Surveys from Asia, vol. 7, Nos. 2-3, pp. 121-132, 2003.
Liu et al., A Simple and Versatile Method for Alkene Epoxidation Using Aqueous Hydrogen Peroxide and Maganese Salophen Catalysts, Tetrahedron Letters, 47, pp. 1923-1926, 2006.
Anilkumar et al., An Efficient Biomimetic Fe-catalyzed Epoxidation of Olefins Using Hydrogen Peroxide, Chemical Communication, pp. 289-291, 2007.
S. Yamakazi, An Improved Methyltrioxorhenium-catalyzed Epoxidation of alkenes with Hydrogen Peroxide, Organic & Biomolecular Chemistry, 5, pp. 2109-2113, 2007.
Edwards et al., Nanocrystalline Gold and Gold-palladium as Effective Catalysts for Selective Oxidation, Materials Research Society, vol. 22, No. 4, pp. 831-837, 2007.
Hayashi et al., Selective Vapor-Phase Epoxidation of Propylene Over Au/TiO2 Catalysts in the Presence of Oxygen and Hydrogen, 178, pp. 566-575, 1998.

* cited by examiner

Primary Examiner — Taylor Victor Oh

(57) ABSTRACT

A process for preparing a divinylarene dioxide comprising reacting a divinylarene, such as divinylbenzene, with hydrogen peroxide in the presence of a solvent and in the presence of a catalyst to from a divinylarene dioxide; wherein the hydrogen peroxide is present in the reaction mixture in an excess or an equivalent mole ratio per mole of divinylarene.

31 Claims, No Drawings ns, particularly divinylbenzene (DVB), are a class of diepoxides which can be used as either reactive diluents or the main epoxy resin matrix in epoxy thermoset formulations. DVBDO itself has a very low liquid viscosity (for example less than about 20 mPa-s) making DVBDO especially useful in the preparation of low viscosity epoxy formulations. The epoxy formulations made from DVBDO are useful as intermediates in the production of various other products for example suitable for use in the fields of coatings, composites, and molding compositions.

PROCESS FOR PREPARING DIVINYLARENE DIOXIDES

CROSS REFERENCE TO RELATED APPLICATIONS

This is a §371 application of PCT International Patent Application Number PCT/US2009/065435 filed Nov. 23, 2009, and claims priority from provisional applications Ser. No. 61/141,457 filed Dec. 30, 2008, which is incorporated herein by reference in its entirety.

BACKGROUND OF THE INVENTION

1. Field of the Invention

The present invention is related to a process for preparing divinylarene dioxides, particularly those derived from divinylbenzene.

2. Description of Background and Related Art

Divinylarene dioxides, particularly divinylbenzene dioxide (DVBDO) and others which are derived from divinylarenes, particularly divinylbenzene (DVB), are a class of diepoxides which can be used as either reactive diluents or the main epoxy resin matrix in epoxy thermoset formulations. DVBDO itself has a very low liquid viscosity (for example less than about 20 mPa-s) making DVBDO especially useful in the preparation of low viscosity epoxy formulations. The epoxy formulations made from DVBDO are useful as intermediates in the production of various other products for example suitable for use in the fields of coatings, composites, and molding compositions.

There are previously known processes for the preparation of DVBDO using hydrogen peroxide ($H_2O_2$). However, none of these previously known prior art processes can produce DVBDO in high yields efficiently and economically. For example, the process described in Inoue et al, Bull. Chem. Soc. Jap., 1991, 64, 3442, employs a molybdenum catalyst and sodium nitrate or sodium sulfate additives providing yields of DVBDO at less than 10% because of product instability and catalyst deactivation. JP 09286750 discloses a process for producing DVBDO at a yield of 30%.

The above processes known in the prior art have not successfully provided DVBDO in high yields (for example greater than 30%). In addition, the prior art processes do not produce DVBDO without co-production of undesirable by-products such as acetamide or acetic acid.

It is therefore desired to provide a process for preparing divinylarene dioxides, particularly those derived from divinylbenzene, using $H_2O_2$ without co-production of undesirable by-products; and wherein the divinylarene dioxide is produced in high yields using an economical and efficient process.

SUMMARY OF THE INVENTION

The present invention is directed to the preparation of divinylarene dioxides using an oxidant such as hydrogen peroxide in the presence of a catalyst and in the presence of a solvent; wherein the process is carried out under conditions such that the co-production of undesirable by-products is minimized or is essentially eliminated. The process of the present invention also advantageously produces divinylarene dioxides in high yields, for example, in yields of greater than about 30%.

In one embodiment of the present invention, a catalyzed epoxidation of a divinylarene with hydrogen peroxide as the oxidizing agent in the presence of a catalyst and a solvent is carried out to form, for example, a divinylarene dioxide such as divinylbenzene dioxide; wherein the hydrogen peroxide is present in the reaction mixture in mole ratio per mole of divinylarene of 2 or more.

As an illustration of the present invention, a divinylbenzene may be dissolved in a solvent such as dichloromethane, and using hydrogen peroxide as the oxidizing agent, a catalyst, for example methyltrioxorhenium (MTO) with an organic modifier such as 3-methylpyrazole (3 MP), may be added to the reaction mixture; and then the reaction may be carried out at a temperature of between about 0° C. to about 100° C.

DETAILED DESCRIPTION OF THE INVENTION

The present invention is not limited to the specific embodiments described below, but rather; the present invention includes all alternatives, modifications, and equivalents falling within the true scope of the appended claims.

In its broadest scope, the present invention comprises a process for preparing a divinylarene dioxide. A divinylarene dioxide of the present invention is prepared by reacting a divinylarene with hydrogen peroxide in the presence of a solvent and in the presence of a catalyst. For example, in one embodiment, a divinylarene dioxide such as divinylbenzene dioxide (DVBDO) is prepared by dissolving a divinylbenzene (DVB) in dichloromethane, using hydrogen peroxide ($H_2O_2$) as the oxidizing agent. A catalyst, for example methyltrioxorhenium (MTO) with 3-methylpyrazole (3 MP) organic modifier, may be added to the reaction mixture; and then the reaction may be carried out at a temperature of between about 0° C. to about 100° C. After the epoxidation is completed the solvent and organic modifier may be removed, and if desired, the product may be purified by known means such as distillation.

In one embodiment, the source of divinylarenes may come from processes which prepare divinylarenes such as for example; divinylarenes can be prepared with salt or metal wastes from arenes and ethylene.

In another embodiment, the divinylarene may consist of any substituted or unsubstituted arene nucleus bearing two vinyl groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of $H_2O_2$-resistant groups including for example saturated alkyl, aryl, halogen, nitro, isocyanate, or RO—(where R may be saturated alkyl or aryl), or mixtures thereof. Ring-annulated benzenes may include for example naphthalene, tetrahydronaphthalene, and the like, and mixtures thereof.

In yet another embodiment, the divinylarene may contain quantities (such as for example less than about 20 weight percent) of substituted arenes. The amount and structure of the substituted arenes depend on the process used in the preparation of the divinylarene. For example, DVB prepared by the dehydrogenation of diethylbenzene (DEB) may contain quantities of ethylvinylbenzene (EVB) and DEB. Upon reaction with hydrogen peroxide, EVB produces ethylvinylbenzene monoxide while DEB remains unchanged.

The divinylarene used in the process of the present invention may include for example divinylbenzene dioxide, divinylnaphthalene dioxide, divinylbiphenyl dioxide, divinyldiphenylether dioxide; and mixtures thereof.

The concentration of the divinylarene used in the present invention may range generally from about 1 weight percent (wt %) to about 100 wt %, preferably from about 2 wt % to about 98 wt %, and more preferably from about 5 wt % to about 95 wt %.

The oxidizing agent used in the process of the present invention is hydrogen peroxide. Hydrogen peroxide may be pre-manufactured or generated in-situ in the course of the reaction with the divinylarene, for example as disclosed in Edwards et al., J. Mater. Res., 22, (4) 831, 2007; or Hayashi et al., J. Catal., 178, 566, 1998. Hydrogen peroxide may also be pre-manufactured using the anthraquinone/tetrahydroanthraquinone process with an appropriate hydrogenation catalyst such as palladium on alumina or Raney nickel such as described in U.S. Pat. No. 3,635,841.

The concentration of the $H_2O_2$ oxidant used in the present invention may range generally from about 0.1 wt % to about 100 wt %, preferably from about 1 wt % to about 80 wt %, and more preferably from about 10 wt % to about 60 wt %.

In one embodiment, an optional solvent may be used in the process of the present invention. The optional solvent useful in the process of the present invention may include for example any inert organic solvent that is inert to $H_2O_2$ under the reaction conditions. For example, the solvent may include halogenated alkanes such as dichloromethane; aromatics such as toluene; polar organic solvents such as dimethyl formamide, or ethers such as tetrahydrofuran; alcohols such as t-amyl alcohol and methanol; or fluorinated alcohols such as trifluoroethanol; or mixtures thereof.

The concentration of the solvent used in the present invention may be in the range of generally from about 1 wt % to about 99 wt %, preferably from about 5 wt % to about 95 wt %, and more preferably from about 10 wt % to about 90 wt %.

The catalyst useful in the process of the present invention may include for example metal oxides such as alkyltrioxorhenium compounds; heteropolyacids such as phosphotungstate compounds; macroporous and mesomorphous zeolites such as titanium silicate compounds; and transition metal complexes of porphyrins, phthalocyanines, and Schiff bases, pyridine and ring annulated pyridine derivatives with at least one or more additional coordinating groups; cyclam; cylen; 8-hydroxyquinoline derivatives and the like; and mixtures thereof, wherein the transition metal may be include for example iron, cobalt, manganese and the like.

In one embodiment, the catalyst of the present invention is methyltrioxorhenium.

In another embodiment, the catalyst of the present invention is in-situ generated or isolated ammonium salts of peroxophosphotungstic acid. These salts can be prepared from tungstic acid or phosphotungstic acid and hydrogen peroxide and ammonium salts. The ammonium salts are detailed below under other/optional components.

In another embodiment, the catalyst of the present invention may be selected from one or more titanium silicate compounds such as TS-1, MCM-41, ZSM-5 or SBA-1. Different transition metals such as Ti, V, Fe, Pd, Nb, Mn, Mo and Cr could be built into the silica frame work to reduce side reactions.

In another embodiment, the catalyst of the present invention is a transition metal complex. The transition metal for the catalyst is selected from the group comprising of iron, manganese, cobalt, vanadium, chromium, copper and mixtures thereof. The chelants may be cyclen, triazanonane, cyclam or their N-alkyl substituted derivatives. The chelants also may be Schiff bases originating from salicylic aldehyde (or alkyl, aryl substituted analogs) and diamines such as ethylene diamine, o-phenylene diamine, 1,2-cyclohexyl diamine and the like. Other variants for chelants are phthalocyanine or porphyrin and their halogen and alkyl or aryl substituted analogs. The chelants could also be pyridine and ring annulated pyridine derivatives with at least one or more additional coordinating groups on any of the rings. The coordinating groups are selected from hydroxyl groups, thiols, carboxylic acid groups or iminium group in which the carbon can be substituted with alkyl, aryl, O-alkyl, O-aryl, N-alkyl, N-aryl, S-alkyl, or S-aryl groups and imine nitrogen can be substituted with alkyl or aryl groups. For example, the chelants with the pyridine and ring annulated pyridine based structures are depicted below, where $R_1$ are carboxylic acid groups, $R_2$ and $R_3$ could be alkyl, aryl, or O-alkyl, O-aryl, N-alkyl, N-aryl, S-alky or S-aryl groups and $R_2$ and $R_3$ could also be part of a ring system. R4 is situated at any ring position of the annulated ring system and selected from halogens, hydroxyl, thiol, alkyl or aryl groups.

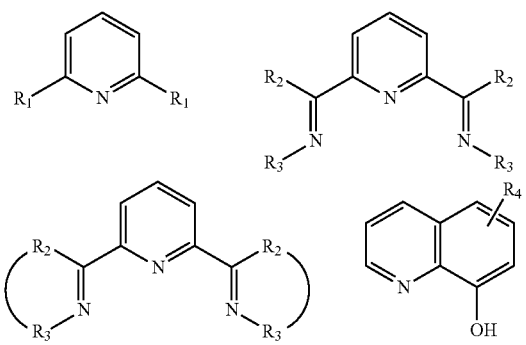

Preferred transition metal complex catalysts of the present invention are iron(III) chloride-2,6-pyridine dicarboxylic acid complex modified with either diisopropylamine or benzylamine and manganese(III) 8-hydroxyquinoline complex and its 5,7-substituted analogs; and mixtures thereof.

There are numerous transition metal complexes of porphyrins, phthalocyanines, and Schiff bases, pyridine carboxylates, 8-hydroxy-quinoline, cyclam, cylen, N,N',N''-triazacyclononane and the like which have been used for the epoxidation of styrene and its derivatives as disclosed in Shrinivas et al., Biomimetic Oxidations Using Transition Metal Complexes Encapsulated in Zeolites, Catalysis Surveys from Asia, vol 7, 2-3, 121-131, 2003. In another embodiment of the present invention, the catalysts described in the above reference may be useful for the epoxidation of DVB and result in high yields and epoxide selectivity. The particular selection of the catalyst depends to some extent on the reaction conditions, since DVB polymerizes much easier than styrene and is more sensitive to acidic and basic conditions. Other catalysts described in the art that may be useful in the present invention include a rhenium based catalyst as disclosed in S. Yamakazi, Org. Biomol. Chem., 2007, 5, 2109; an Fe complex catalyst as disclosed in Anilkumar et al., An Efficient Biomimetic Fe-catalyzed Epoxidation of Olefins Using Hydrogen Peroxide, Chem. Commun., 289-291, (2007). al.; and a manganese salophen catalyzed epoxidation as disclosed in Liu et al., A Simple and Versatile Method for Alkene Epoxidation Using Aqueous Hydrogen Peroxide and Manganese Salophen Catalysts, Tetrahedron Lett., 47, 1923, 2006. The above references all are incorporated herein by reference.

The concentration of the catalyst used in the present invention may range generally from about 0.001 wt % to about 5 wt %, preferably from about 0.01 wt % to about 1 wt %, and more preferably from about .0.1 wt % to about 0.5 wt %.

An organic modifier may optionally be used in the process of the present invention including for example Lewis bases such as N-containing compounds; either alicyclic amines such as triethyl amine, ethylene diamine, benzyl amine or diisopropyl amine, or heterocyclic amines like pyrazole, pyridine, bipyridine, N,N-dimethylaminopyridine, diazobicyclooctane (DABCO) and their derivatives; N-oxides, alkyl or cyano-substituted analogs; and mixtures thereof.

The optional organic modifier may depend on the catalyst used in the process of the present invention. For example, when an alkyltrioxorhenium catalyst is used, the organic modifier may include a tertiary amine such as a pyridine or a pyrazole. The amines may be alkyl or aryl substituted at any ring position.

When a phosphotungstate catalyst is used in the present invention, the organic modifier may be a tertiary amine, ammonium salt, or a quaternary ammonium salt such as methyl-trioctylamine hydrogen sulfate, ammonium salts containing methyl or benzyl groups and long aliphatic hydrocarbon chains ($C_{10}$-$C_{18}$), tricaprylammonium chloride, tributylhexadecylammonium bromide, benzalkonium chloride and the like; and mixtures thereof.

When a manganese porphyrin catalyst is used in the present invention, the organic modifier may be a carboxylic acid, an ammonium carboxylate, or a carboxylic acid anhydride; and mixtures thereof.

When an iron porphyrin catalyst is used in the present invention, the organic modifier may be for example (though not limited to), an aliphatic amine or an imidazole.

When Schiff bases or pyridine carboxylates or hydroxyquinolines are used additional Lewis bases or, N-heterocycles can be used for example pyrazole and pyrrolidine or carboxylate salts such as ammonium acetate or acetic acid; and mixtures thereof.

The concentration of the organic modifier used in the present invention may range generally from about 0.01 wt % to about 30 wt %, preferably from about 0.1 wt % to about 20 wt %, and more preferably from about 1 wt % to about 10 wt %.

In another embodiment of the present invention, the organic modifier may be added to the composition of the present invention to assist in the reaction process; and subsequently, the organic modifier may be removed, if desired, after its use. For example, after the reaction step, the resulting divinylarene dioxide reaction product is isolated and the concentration of the organic modifier in the reaction product is reduced to about 5 weight percent or less; and preferably the concentration of the organic modifier is reduced to about 0.5 weight percent or less. In one embodiment the concentration of the organic modifier is from about 0.004 weight percent to about 5 weight percent; more preferably the concentration of the organic modifier is from about 0.01 weight percent to about 5 weight percent; and most preferably the concentration of the organic modifier is from about 0.5 weight percent to about 1.5 weight percent.

An assortment of optional additives may be added to the composition of the present invention including for example, other resins, stabilizers, fillers, plasticizers, catalyst de-activators, and the like; and mixtures thereof.

The concentration of the optional additives used in the present invention may range generally from 0 wt % to about 99.9 wt %, preferably from about 0.1 wt % to about 99.9 wt %, more preferably from about 1 wt % to about 99 wt %, and most preferably from about 2 wt % to about 98 wt %. In another embodiment the additives may be from about 0.01 wt % to about 99.9 wt %.

The preparation of divinylarene dioxides using $H_2O_2$ without co-production of undesirable by-products may be achieved by (i) adding to a reactor the following reactants: a divinylarene, a catalyst, optionally an organic modifier, and optionally an inert organic solvent; (ii) contacting the reactants with $H_2O_2$; and then allowing the reactant components to react under reaction conditions to produce the corresponding divinylarene dioxide.

The reaction of the divinylarene with the $H_2O_2$ is carried out with an excess of or an equivalent moles of $H_2O_2$. Generally, the reaction is carried out at a $H_2O_2$:divinylarene mole ratio of at least 2 or more; preferably, from about 2 to about 50; more preferably, from about 2 to about 10; and most preferably, from about 2 to about 4 mole ratio. If less than two moles of $H_2O_2$ per mole of divinylarene is used, there would not be sufficient amount of oxidizing agent to epoxidize both of the double bonds in the divinylarene. For example, using one mol $H_2O_2$ could provide a product that contains one epoxide group and one double bond on average. In addition, if less than 2 mol $H_2O_2$ per mole of divinylarene is used, the resulting reaction product may be unstable, i.e., the product may have an increase in viscosity, and ultimately may gel prior to reaction with an epoxy curing agent. If above 50 moles of $H_2O_2$ per mole of divinylarene is used, the benefits of using the $H_2O_2$ oxidant in the reaction may no longer be economical; and use of more $H_2O_2$ oxidant may be wasteful.

The reaction conditions include carrying out the reaction under a temperature, generally in the range of from about 0° C. to about 100° C., preferably from about 5° C. to about 80° C., and more preferably from about 20° C. to about 60° C.

The pressure of the reaction may be generally from about 0.1 atmosphere (atm) to about 10 atm.

The reaction process of the present invention may be a batch or a continuous process. The reactor used in the process may be any reactor and ancillary equipment well known to those skilled in the art.

During the reaction for the preparation of divinylarene dioxides, water is co-produced. The use of $H_2O_2$ as the oxidant forms water as the only oxidant by-product. Undesirable by-products from solvents, oxidants, or modifiers such as acetamide and acetic acid are not formed to any substantial degree in the reaction of the present invention as found in the prior art processes. Other undesirable oxidized by-products and derivatives, such as for example carbonyl compounds and hydrolyzed epoxy products, are also not formed in any appreciable quantities using the process of the present invention.

In the process of the present invention, the insubstantial quantities of the undesirable by-products produced in the reaction of the present invention, are generally, less than about 20 wt % of undesirable by-products; preferably, less than about 10 wt %; more preferably, less than about 5 wt %; and most preferably zero wt % undesirable by-products.

After the reaction of the present invention, the co-produced water; and any remaining organic modifier, catalyst, and solvent, may be removed to recover a usable divinylarene dioxide product. Then the product may optionally be purified by well-known means in the art such as by distillation, crystallization, and the like.

One advantage of the present invention process is that high yields of divinylarene dioxides may be produced by the process of the present invention. With high yields of divinylarene dioxides produced, the process of the present invention advantageously requires less recycle and produces less waste.

The "high yield" of the divinylarene dioxides produced by the process of the present invention, is generally greater than about 30%; and preferably, ranges from about 70% to about 100%; more preferably, from about 80% to about 100%; and most preferably, from about 90% to about 100% based on divinylarene starting material.

The divinylarene dioxides prepared by the process of the present invention, particularly those derived from divinylbenzene such as for example divinylbenzene dioxide (DVBDO), are class of diepoxides which have a relatively low liquid viscosity but a higher rigidity than conventional epoxy resins.

The divinylarene dioxide prepared by the process of the present invention may comprise, for example, any substituted or unsubstituted arene nucleus bearing two vinyl groups in any ring position. The arene portion of the divinylarene dioxide may consist of benzene, substituted benzenes, or (substituted) ring-annulated benzenes or homologously bonded (substituted) benzenes, or mixtures thereof. The divinylbenzene portion of the divinylarene dioxide may be ortho, meta, or para isomers or any mixture thereof. Additional substituents may consist of $H_2O_2$-resistant groups including saturated alkyl, aryl, halogen, nitro, isocyanate, or RO—(where R may be a saturated alkyl or aryl). Ring-annulated benzenes may consist of naphthalene, tetrahydronaphthalene, and the like. Homologously bonded (substituted) benzenes may consist of biphenyl, diphenylether, and the like.

The divinylarene oxide product prepared by the process of the present invention may be illustrated generally by general chemical Structures 1-IV as follows:

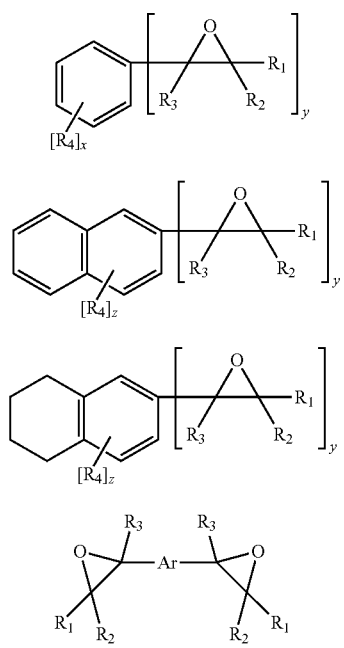

In the above Structures I, II, III and IV of the divinylarene dioxide product of the present invention, each $R_1$, $R_2$, $R_3$ and $R_4$ individually may be hydrogen, an alkyl, cycloalkyl, an aryl or an aralkyl group; or a $H_2O_2$-resistant group including for example a halogen, a nitro, an isocyanate, or an RO group, wherein R may be an alkyl, aryl or aralkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, 1,3-phenylene group.

The divinylarene dioxide product produced by the process of the present invention may include for example alkyl-vinyl-arene monoxides depending on the presence of alkylvinylarene in the starting material.

In one embodiment of the present invention, the divinylarene dioxide produced by the process of the present invention may include for example divinylbenzene dioxide, divinylnaphthalene dioxide, divinylbiphenyl dioxide, divinyldiphenylether dioxide, and mixtures thereof.

Structure V below illustrates an embodiment of a preferred chemical structure of a divinylbenzene dioxide (DVBDO) useful in the present invention:

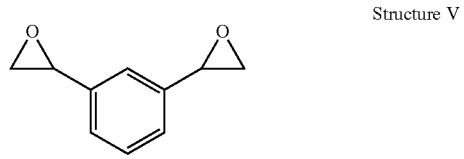 [SMILES: c1cc(C2CO2)cc(C2CO2)c1]

Structure VI below illustrates another embodiment of a preferred chemical structure of the DVBDO useful in the present invention:

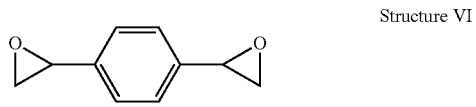

When DVBDO is prepared by the process of the present invention, it is possible to obtain one of three possible isomers: ortho, meta, and para. Accordingly, the present invention includes a DVBDO illustrated by any one of the above Structures individually or as a mixture thereof. Structures V and VI above show the meta (1,3-DVBDO) and para (1,4-DVBDO) isomers of DVBDO, respectively. The ortho isomer is rare; and usually a mixture of DVBDO is mostly produced as an about 2:1 ratio of meta (Structure V) to para (Structure VI). Thus, the present invention preferably includes as one embodiment an about 2:1 ratio of Structure V to Structure VI.

In one embodiment, the process of the present invention is particularly suited for the preparation of divinylbenzene dioxide, a low viscosity liquid epoxy resin. The viscosity of the divinylarene dioxides produced by the process of the present invention ranges generally from about 10 mPa-s to about 100 mPa-s; preferably, from about 10 mPa-s to about 50 mPa-s; and more preferably, from about 10 mPa-s to about 25 mPa-s at 25° C.

The utility of the divinylarene dioxides of the present invention requires their thermal stability to allow their formulation or processing at moderate temperatures (for example, at from about 100° C. to about 200° C.) for up to several hours (for example, for at least 2 hours) without oligomerization or homopolymerization. Oligomerization or homopolymerization during formulation or processing is evident by a substantial increase in viscosity or gelling (crosslinking). The divinylarene dioxides of the present invention have sufficient thermal stability such that they do not experience a substantial increase in viscosity or gelling during formulation or processing at moderate temperatures.

EXAMPLES

The following examples and comparative examples further illustrate the present invention in detail but are not to be construed to limit the scope thereof.

Various terms and designations used in the following examples are explained as follows: "DVB" stands for divinylbenzene; "DVBO" stands for divinylbenzeneoxide; "DVBDO" stands for divinylbenzene dioxide; "EVB" stands for ethylvinylbenzene; "3-MP" stands for 3-methylpyrazole; "MTO" stands for methyltrioxorhenium; "HQ" stands for 8-hydroxyquinoline; Aliquat 336 (tricaprylmethyl ammonium chloride) is commercially available from Sigma-Aldrich.

The product mixtures prepared in the Examples which follow were analyzed by standard gas chromatography (GC) analytical equipment and methods.

Example 1

DVB (1 g, 7.68 mmol, 80% DVB, 20% EVB), 3-MP (0.126 g, 1.54 mmol) and MTO (19.1 mg, $7.68 \times 10^{-2}$ mmol) were dissolved in 10 mL dichloromethane and vigorously stirred in a three-neck flask equipped with a condenser, thermometer and an addition funnel. Hydrogen peroxide (31%, 3.370 g, 30.7 mmol) was added drop wise in the course of 15 minutes and the temperature was kept around 25° C. by cooling the flask in a water bath. The reaction mixture was vigorously stirred and further incubated at 25° C. The progress of the reaction was monitored by gas chromatography. After 8 hours no more starting material and mono-epoxidized DVB were present.

The resulting aqueous and organic phases were separated. The organic phase was washed with sodium thiosulfate solution (0.25 M) followed by washing with phosphoric acid (1M) and water. Disregarding the EVB content in the starting material, the desired product, DVBDO, was isolated in 70% yield.

Example 2

The heat stability of DVBDO was assessed by incubating the product at 140° C. and observing if viscosity increase/polymerization occurred. Table I below summarizes how 3-MP concentration in the product affected heat stability.

TABLE I

| 3-MP concentration (wt %) | Incubation time (hours) | Observations |
|---|---|---|
| 5 | 0.5 | Sample solidified (crosslinked) |
| 1.7 | 1 | Significant viscosity increase |
| 0.5 | 2 | No viscosity increase |

Example 3

Phosphotungstic acid ($H_3\{PO_4(WO_3)_{12}\}$, 0.1 g, 0.03 mmol) was dissolved in water (1 mL). Phosphoric acid (30%, 0.022 g, 0.07 mmol) was added, followed by $H_2O_2$ (29%, 0.102 g 0.9 mmol). The reaction mixture was stirred at 20° C. for 30 minutes when Aliquat 336 (0.126 g, 0.3 mmol) was added in dichloroethane solution (5 mL). The reaction mixture was stirred at 20° C. for 20 minutes. Then DVB (1 g, 8 mmol, 80% DVB, 20% EVB) in dichloroethane solution (5 mL) was added and the temperature was raised to 50° C. $H_2O_2$ (29%, 3.6 g, 32 mmol) was added to the mixture dropwise. The reaction mixture was stirred at this temperature for 6 hours. The reaction mixture was worked up as described in Example 1. A resultant DVBDO product was formed in 20% yield.

Example 4

$FeCl_3$ hexahydrate (0.025 mmol) and 2,6-pyridine dicarboxylic acid (0.025 mmol) were mixed in t-amyl alcohol (9 mL) in each of four 20 mL vials equipped with a magnetic stirbar. After stirring 15 minutes, diisopropylamine (3.5 µL, 7.0 µL and 10.5 µL; 0.025, 0.05 and 0.75 mmol, respectively) were added to three separate vials. One vial had no additional amine added to act as a control. To each of the four vials was also added dodecane (57 µL, 0.25 mmol) as an internal standard. The resulting solutions were allowed to stir an additional 30 minutes. Then 95% DVB (71.1 µL, 0.5 mmol) was added to each of the reaction vials. This was followed by rapid addition of 30% $H_2O_2$ (228 µL, 2 mmol). The resulting reaction mixtures were allowed to stir at ambient temperature, no attempt being made to control any exotherm which occurred upon addition. At 45 minutes and again at 3 hours after addition of the peroxide, samples (0.25 mL) were removed and analyzed by gas chromatography. Except for the control (no amine added) no peroxide remained at the end of the reaction (3 hours) as indicated by peroxide test strips. The samples were analyzed for the following properties described in Table II.

TABLE II

| Equiv. iPr$_2$NH | Rxn time (minutes) | DVB conversion (%) | DVBDO selectivity (%) |
|---|---|---|---|
| 0 | 45 | 8 | 0 [a] |
| 1 | 45 | 100 | 77 [b] |
|   | 180 | 100 | 73 [b] |
| 2 | 45 | 100 | 71 [b] |
|   | 180 | 100 | 72 [b] |
| 3 | 45 | 88 | 30 [c] |

[a] No reaction products of any sort detected.
[b] 1-3% selectivity for monoepoxide observed.
[c] 60% selectivity for monoepoxide observed Example 5

Mn(III) complexes were prepared by a literature procedure described in (J. of Catalysis, 256, 154, 2008). A general procedure for testing the manganese(III) complexes of HQ and its halogen substituted analogs is given here. DVB (1 mmol, 80% DVB, 20% EVB), catalyst (0.04 mmol), additives, and acetone (3 mL) were transferred into a vial. Ammonium acetate (0.1 mmol) and glacial acetic acid (0.2 mmol) either together or separately were used as additives. Into this mixture hydrogen peroxide (30%, 3 mmol) was added in 5 aliquots in the course of 15 minutes. The reaction mixture was stirred at 25° C. for three hours and analyzed by GC. The results are summarized in Table III as follows:

TABLE III

| Chelant | Additive | DVB (area %) | DVBO (area %) | DVBDO (area %) |
|---|---|---|---|---|
| HQ | Ammonium acetate and acetic acid | 27 | 35 | 18 |
| HQ | Acetic acid | 17 | 35 | 18 |
| 5,7-dichloro-HQ | Ammonium acetate and acetic acid | 18 | 33 | 12 |
| 5,7-dibromo-HQ | Ammonium acetate and acetic acid | 22 | 31 | 17 |

The process of the present invention is not to be limited by the specific examples set forth above including the tables to which they refer. Rather, the above examples and the tables they refer to are illustrative of the process of the present invention.

What is claimed is:

1. A process for preparing a divinylarene dioxide comprising the steps of:
   (a) reacting a divinylarene with hydrogen peroxide in the presence of a catalyst and in the presence of an organic modifier to form a divinylarene dioxide; wherein the hydrogen peroxide is present in an excess or an equivalent mole ratio per mole of vinyl group; wherein the organic modifier is a Lewis base; and wherein the divinylarene dioxide is produced at a yield of greater than 30 percent yield; and
   (b) reducing the organic modifier concentration in the divinylarene dioxide produced in step (a); wherein the concentration of the organic modifier in the divinylarene dioxide is reduced to about 5 weight percent or less.

2. The process of claim 1, wherein the reaction is carried out at a mole ratio of hydrogen peroxide:divinylarene dioxide of at least 2 or more.

3. The process of claim 1, wherein hydrogen peroxide is generated in-situ using hydrogen and oxygen; or wherein hydrogen peroxide is generated in-situ using an anthraquinone/tetrahydroanthraquinone process in the presence of a hydrogenation catalyst.

4. The process of claim 3, wherein the hydrogenation catalyst comprises palladium; alumina; Raney nickel; or mixtures thereof.

5. The process of claim 1, wherein the catalyst is selected from the group consisting of a titanium dioxide-gold catalyst; a gold catalyst supported on a non-porous and mesoporous titania-silica; a metal oxide; a transition metal complex; and a heteropolyacid.

6. The process of claim 5, wherein the silica component of the catalyst is selected from the group consisting of natural zeolites, synthetic zeolites, and mixtures thereof.

7. The process of claim 1, wherein the divinylarene is divinylbenzene; and wherein the divinylarene dioxide formed is divinylbenzene dioxide.

8. The process of claim 1, wherein the reaction is carried out at a temperature within the range of from about 5° C. to about 80° C.

9. The process of claim 1 wherein the catalyst is selected from the group consisting of methyltrioxorhenium; a cobalt salen complex; a manganese salen complex; a manganese-chelant complex; an iron-chelant complex; an iron porphyrin; a manganese porphyrin; and a phosphotungstic acid ammonium salt.

10. The process of claim 9, wherein the chelant of the manganese complex or the iron complex is pyridine or a ring annulated pyridine compound with at least one or more additional coordinating groups on any of the rings.

11. The process of claim 10, wherein the coordinating groups comprise hydroxyl or thiol groups.

12. The process of claim 9 including salen chelants originating from alkyl, aryl, o-alkyl, O-aryl or halogen substituted salicylic aldehyde.

13. The process of claim 9, wherein the ammonium ion comprises tetrabutyl ammonium salts; ammonium salts with one or two long alkyl chains having longer than C8 chains; methyl pyridinium groups, benzyl pyridinium groups, cetylpyridinium groups; or mixtures thereof.

14. The process of claim 9, wherein the catalyst is immobilized on a solid support.

15. The process of claim 14, wherein the solid support comprises zeolites, clays, silica, alumina, or polymers.

16. The process of claim 1, wherein the concentration of said catalyst ranges from about 0.001 weight percent to about 5 weight percent; wherein the concentration of said divinylarene ranges from about 1 weight percent to about 100 weight percent; and wherein the hydrogen peroxide concentration ranges from about 0.1 weight percent to about 100 weight percent.

17. The process of claim 1 including a solvent; wherein the solvent comprises chlorinated hydrocarbons; aromatic hydrocarbons; polar solvents; ethers; alcohols; fluorinated alcohols; or mixtures thereof.

18. The process of claim 17, wherein the chlorinated hydrocarbons comprise dichloromethane or dichloroethane; wherein the aromatic hydrocarbons comprise benzene or toluene; wherein the polar solvents comprise dimethyl formamide; wherein the ethers comprises tetrahydrofuran; or wherein the alcohols or fluorinated alcohols comprise i-amylalcohol or trifluoroethanol.

19. The process of claim 1, wherein the concentration of said solvent ranges from 0.01 weight percent to about 99 weight percent.

20. The process of claim 1, wherein the Lewis base is selected from the group consisting of an N-oxide, acetic acid, salts of acetic acid, and mixtures thereof.

21. The process of claim 20, wherein the Lewis base is selected from the group consisting of pyrazole, pyridine, pyrrolidine, bipyridine, imidazole, benzylamine, diisopropylamine, a Lewis base containing an alkyl or an aryl group and mixtures thereof.

22. The process of claim 20, wherein the N-oxide is pyridine-N-oxide.

23. The process of claim 1, wherein after the reaction step, the resulting divinylarene dioxide reaction product is isolated and purified.

24. The process of claim 23, wherein the divinylarene dioxide reaction product is purified by distillation.

25. The process of claim 10, wherein the coordinating groups are 8-hydroxyquinoline.

26. The process of claim 10, wherein the coordinating groups are carboxylic acid groups.

27. The process of claim 26, wherein the coordinating groups are 2,6-pyridinedicarboxylic acid.

28. The process of claim 10, wherein the coordinating groups are iminium groups wherein the carbon atom in the iminium groups can be an alkyl, an aryl, an O-alkyl, an O-aryl, a N-alkyl, a N-aryl, a S-alkyl or a S-aryl group.

29. The process of claim 10, wherein the coordinating groups are an imine nitrogen, an alkyl group or an aryl group.

30. The process of claim 9 including diamines selected from the group consisting of ethylene diamine; 1,2 cyclohexyl diamine: 1,2-phenylenediamine; and diamines substituted with alkyl, aryl or halogen.

31. The process of claim 15, wherein the polymer solid support is selected from the group consisting of polyglycerol, polystyrene, polymethacrylates, dendrimers, and polyvinylpyridine.

* * * * *